United States Patent
Wei et al.

(10) Patent No.: US 7,349,760 B2
(45) Date of Patent: Mar. 25, 2008

(54) SYSTEM AND METHOD FOR SENSING AND CONTROLLING THE CONCENTRATION OF A CHEMICAL AGENT IN A SOLUTION

(75) Inventors: Guang-jong Jason Wei, Mendota Heights, MN (US); Tim Gutzmann, Eagan, MN (US); Paul Schacht, Oakdale, MN (US); Tom Batcher, Mendota Heights, MN (US)

(73) Assignee: Ecolab Inc., Saint Paul, MN (US)

( * ) Notice: Subject to any disclaimer, the term of this patent is extended or adjusted under 35 U.S.C. 154(b) by 1011 days.

(21) Appl. No.: 10/099,494

(22) Filed: Mar. 13, 2002

(65) Prior Publication Data

US 2003/0175983 A1 Sep. 18, 2003

(51) Int. Cl.
G05B 21/00 (2006.01)
G01N 31/16 (2006.01)
G01N 15/06 (2006.01)
G01N 33/00 (2006.01)
G01N 33/48 (2006.01)

(52) U.S. Cl. .................. 700/267; 422/50; 422/68.1; 422/75; 436/50; 436/51; 436/43; 73/1.01; 73/1.02; 73/1.36; 73/1.41; 73/1.57; 73/1.71; 73/1.72; 356/24; 356/25; 356/29; 700/1; 700/28; 700/266; 702/1; 702/22; 702/23

(58) Field of Classification Search .............. 422/50, 422/68.1, 75, 919, 930; 436/50, 51, 43; 73/1.01, 73/1.02, 1.36, 1.41, 1.57, 1.71, 1.72, 1.73, 73/1.74, 1.56, 53.01, 61.56, 61.48; 356/29, 356/24, 25; 700/1, 28, 266, 267; 702/1, 702/22, 23
See application file for complete search history.

(56) References Cited

U.S. PATENT DOCUMENTS 3,647,668 A    3/1972   Lindblad et al.

(Continued)

FOREIGN PATENT DOCUMENTS

AU         8433209        3/1985

(Continued)

OTHER PUBLICATIONS

Dindune A, et al.*Automatic potentiometric titrator for studying the structure of condensed jphosphates*. Izv. Akad. Nauk SSR, Neorg. Mater. (1973), 9 (1), 162-3.

(Continued)

*Primary Examiner*—Brian Sines
(74) *Attorney, Agent, or Firm*—Shumaker & Sieffert, P.A.

(57) ABSTRACT

A system for measuring and controlling the concentration of a chemical agent in a solution has a reaction cell for receiving a sample, a titrant dropper for releasing one or more drops of titrant into the sample, a first photosensor for sensing disruptions of light for every drop of titrant released, and a controller that communicates with the photosensor and computes the concentration of the chemical agent based on the number of disruptions of light at the photosensor. The present invention also includes a method for sensing and controlling the concentration of a chemical agent in a solution. The method includes having a sample containing the chemical agent, triggering the release of a number of drops of titrant into the sample, detecting the number of drops released into the sample, and computing the concentration of the chemical agent in the sample based on the number of drops of titrant released into the sample.

27 Claims, 6 Drawing Sheets

U.S. PATENT DOCUMENTS

| | | | |
|---|---|---|---|
| 3,723,062 A * | 3/1973 | Dahms | 436/51 |
| 4,053,743 A * | 10/1977 | Niemi | 700/267 |
| 4,180,440 A | 12/1979 | Gibboney et al. | |
| 4,203,156 A * | 5/1980 | Ishikawa | 700/267 |
| 4,297,105 A * | 10/1981 | Dube | 436/61 |
| 4,302,299 A * | 11/1981 | Ishikawa | 205/787.5 |
| 4,314,484 A * | 2/1982 | Bowman | 73/861.41 |
| 4,476,095 A * | 10/1984 | Scott et al. | 422/75 |
| 4,509,543 A | 4/1985 | Livingston et al. | |
| 4,635,281 A * | 1/1987 | Jones | 377/21 |
| 4,749,552 A * | 6/1988 | Sakisako et al. | 422/75 |
| 4,756,321 A | 7/1988 | Livingston et al. | |
| 4,865,992 A * | 9/1989 | Hach et al. | 436/51 |
| 4,950,610 A * | 8/1990 | Tittle | 436/163 |
| 5,014,211 A | 5/1991 | Turner et al. | |
| 5,038,807 A | 8/1991 | Bailey et al. | |
| 5,104,527 A * | 4/1992 | Clinkenbeard | 210/94 |
| 5,192,509 A * | 3/1993 | Surjaatmadja et al. | 422/75 |
| 5,364,510 A * | 11/1994 | Carpio | 134/2 |
| 5,404,893 A | 4/1995 | Brady et al. | |
| 5,415,641 A * | 5/1995 | Yerlikaya et al. | 604/251 |
| 5,556,478 A | 9/1996 | Brady et al. | |
| 5,674,538 A | 10/1997 | Lokkesmoe et al. | |
| 5,683,724 A | 11/1997 | Hei et al. | |
| 6,082,204 A | 7/2000 | Munderloh | |
| 6,133,555 A | 10/2000 | Brenn | |
| 2001/0039501 A1 | 11/2001 | Crevel et al. | |
| 2001/0047214 A1 | 11/2001 | Cocking et al. | |
| 2001/0053939 A1 | 12/2001 | Crevel et al. | |
| 2001/0054038 A1 | 12/2001 | Crevel et al. | |

FOREIGN PATENT DOCUMENTS

| | | |
|---|---|---|
| GB | 1212890 | 3/1972 |
| JP | 63009618 | 1/1988 |
| JP | 3137562 | 6/1991 |

OTHER PUBLICATIONS

Lisowski, Zenon. *Device for titration with two polarized electrodes and pHmeter*. Chem. Anal. (Warsaw) (1969), 14 (4), 953-4.

Olsen, Eugene D.; Walton, Roger D., *Automation of amperometric titrations with rotating Pt electrodes*. J. Chem. Educ. (1966), 43 (12), 659-60.

Heath P., *A titrator with a digital display. Lab. Pract.* (1981),30 (9), 881-3.

Volkov, VI, et al. Semiautomatic tranporter-type titrimeter. Zavod. Lab. (1968), 34 (3) 367.

* cited by examiner $$CH_3COOOH + 3I^- + 2H^+ \rightarrow CH_3COOH + H_2O + I_3^-$$

$$I_3^- + STARCH \rightarrow I_3^-/STARCH\ COMPLEX\ (DARK\ BLUE)$$

$$I_3^-/STARCH + 2S_2O_3^{2-} \rightarrow 3I^- + S_4O_6^{2-}\ (COLORLESS)$$

FIG. 2

SYSTEM AND METHOD FOR SENSING AND CONTROLLING THE CONCENTRATION OF A CHEMICAL AGENT IN A SOLUTION

FIELD OF THE INVENTION

This application relates generally to the detection of a chemical agent in a solution and more particularly to a system and method for controlling the levels of a biocide in process water.

BACKGROUND OF THE INVENTION

Chemical agents are used as detergents, disinfectants, food additives, medicinal agents, etc. Use of these agents is often tied to the concentration of the chemical agent in a solution, i.e., the required concentration of the agent needed to accomplish the target use. It is therefore important to both measure and control the concentration of an agent in a solution during its use. For example, biocides are used to disinfect surfaces in the food and beverage industry, i.e., used in the cleaning and disinfecting of food surfaces, such as fruits and vegetables, food contact surfaces, such as counter tops and dishware, and in the cleaning and disinfecting of the inside surfaces of polyethylene telephthalate (PET) bottles. It is critical that a biocide be delivered to the target at a proper use concentration. Delivery of an insufficient amount of biocide may result in the target being tainted with possible hazardous levels of microbes and/or may result in the user violating certain predetermined regulatory requirements, causing the user to be fined or suspended by the relevant regulatory agency. Alternatively, delivery of an excessive amount of a biocide to a target may have a toxic effect on the field worker and/or consumer of the treated product, i.e., from fumes, skin contact or consumption. Further, excessive levels of biocide add unnecessary cost to the disinfection process, i.e., the biocide costs money, and a higher than necessary concentration of biocide may result in increased corrosion to delivery equipment thereby reducing the equipment's life expediency and potentially increasing maintenance costs. Therefore, it is of great importance to accurately monitor and determine the concentration of a chemical agent being delivered to a target over the time period of its target use, and to have the ability to modify the agent's concentration during that same time period.

One common technique for determining the concentration of a chemical agent in a solution is through the use of a manual titration kit. Here, a field worker manually takes a sampling of the solution having the target chemical agent that is being tested, adds an indicator agent to the sample and then adds titrant in a drop wise fashion until the approximate endpoint of the chemical reaction has been reached (the endpoint being a detectable point at which the concentration of the chemical agent is determined from the amount of titrant added, as discussed in greater detail below). The manual titration process tends to be fairly inaccurate because the amounts of sample solution, indicator agent and titrant can vary significantly with manual delivery, and the detection of the endpoint can vary significantly with manual detection. As a result, manual titration of a chemical agent's concentration of any two identical solution samples may vary as much as 20 to 50% by a typical worker in the plant. This variation in results is often unacceptable, as it continues to leave a large amount of uncertainty with regard to the target chemical agent's true concentration.

Furthermore, manual detection is labor intensive and time consuming. On average, a field worker may test a solution every hour or two, requiring the field worker to travel to and perform the titration. In addition, it is difficult to ensure a constant concentration or control of chemical if it is being measured and tracked only every 1 to 2 hours.

A recent attempt has been made to automate the processes used to detect chemical agents in a solution. A syringe mixing device draws a sample from the solution into a syringe and then draws titrant into the syringe until the endpoint of the reaction is reached. However, the equipment required in this approach is expensive, and the added accuracy and precision unnecessary.

Against this backdrop the present invention has been developed.

SUMMARY OF THE INVENTION

Above problems are solved by a method for determining the concentration of a chemical agent in a source. The method includes receiving a sample from the source that contains the chemical agent, triggering the release of a number of drops of titrant into the sample, detecting the number of drops of titrant released into the sample and computing the concentration of the chemical agent in the sample source based on a change in a characteristic of the sample, for example, optical characteristics, oxidation-reduction potential, tracer element concentration, and pH, where the characteristic is dependent on the number of drops of titrant released into the sample. The above problems are further solved by a system for determining the concentration of a chemical agent in a sample, of tracking the concentration of the chemical agent in the sample, and of taking corrective action.

The system includes a reaction cell for receiving a sample from a source, a titrant dropper for releasing one or more drops of titrant into the sample in the reaction cell, a first photosensor for receiving light from a light source where the photosensor senses a disruption in the light for every drop of titrant released by the titrant dropper into the reaction cell, an instrument for detecting or sensing a change in the sample, for example a second photosensor, and a controller for communicating with the detection instrument where the controller determines the concentration of the chemical agent in the sample from the data it receives from the detection instrument and the number of light disruptions detected by the first photosensor. Further, the system can include a dosing pump for controlling the concentration of the chemical agent and a user interface for alerting a user of the determined concentration of the chemical agent.

These and various other features as well as advantages which characterize the present invention will be apparent from a reading of the following detailed description and a review of the associated drawings.

BRIEF DESCRIPTION OF THE DRAWINGS

FIG. 2 illustrates an exemplary titration reaction in accordance with the present invention.

DETAILED DESCRIPTION

Figure 1:
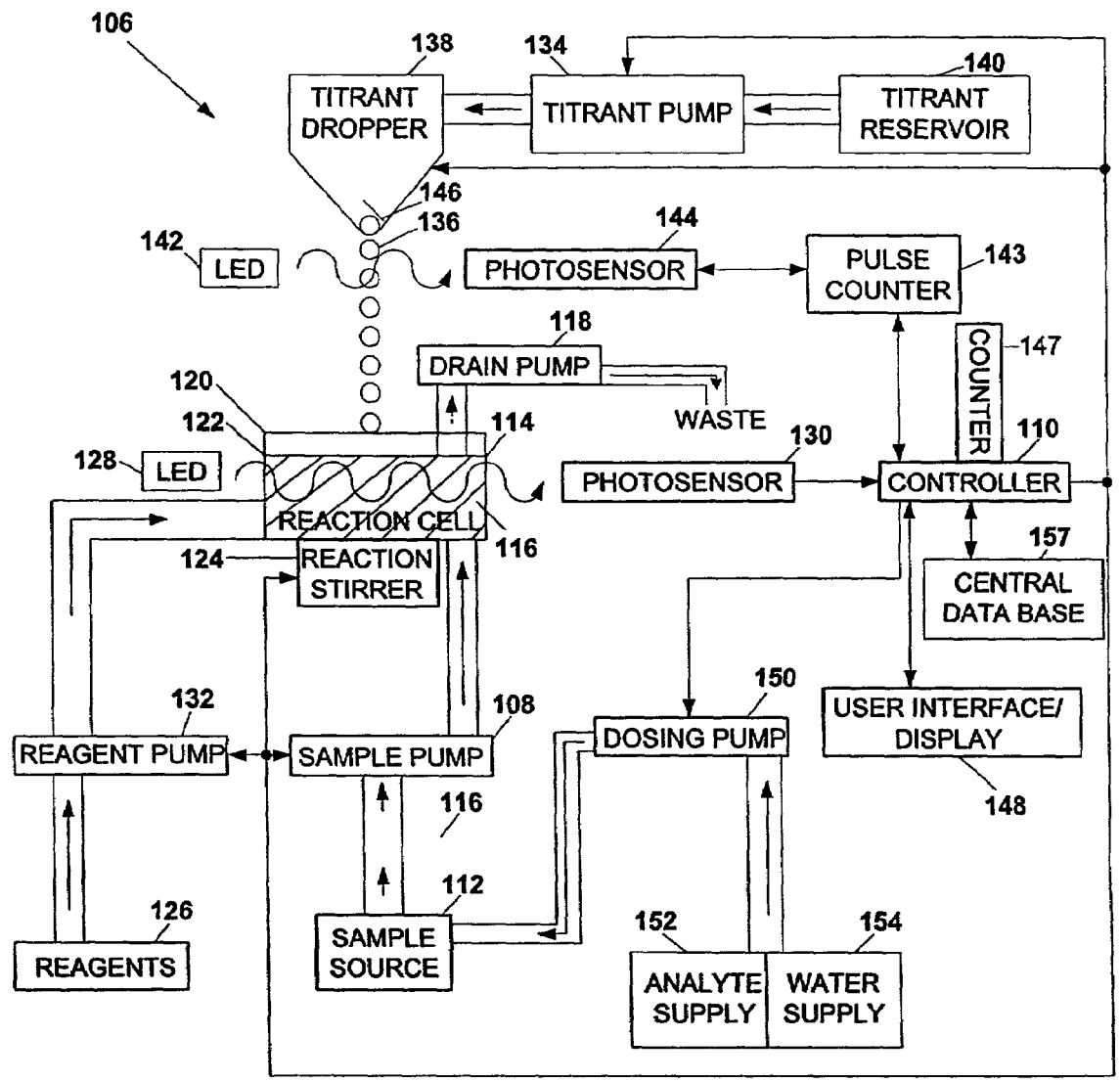
FIG. 1 illustrates an embodiment of the system for controlling the concentration of a target chemical agent in a solution in accordance with the present invention.

Embodiments of the present invention control the concentration of a chemical agent in a source. For example, embodiments of the present invention may be used to control the concentration of a biocide in process water at a fruit and vegetable processing plant, where a biocide is used to reduce or eliminate any microbes resident on the fruits and vegetables before sale and consumption by the public. As such, an embodiment of the present invention detects and modifies, i.e., controls, the biocide concentration in the process water so that a proper concentration of biocide is maintained in the process water and, therefore, is applied to the fruits and vegetables. A further example of an embodiment of the present invention may be used to control the biocide concentration in solutions used to disinfect the internal surfaces of polyethylene telephthalate bottles. Other uses for the methods and systems for controlling a concentration of a chemical agent in a source are envisioned, and are within the scope of the present invention.

Aspects of the invention are based on detecting a target chemical agent's concentration in a solution by using volumetric titration. As known in the art, volumetric titration is based on analyzing a composition, i.e., a chemical agent, of a solution by adding known amounts of a standardized solution until a given reaction (for example, change in an optical characteristic, precipitation, change in conductivity, change in pH, and the like) is produced. For purposes of illustration, the present invention will be described using a change in an optical characteristic, for example a color change, to signal the given reaction. However, other titration reactions are envisioned to be within the scope of the present invention, for example, using a pH meter to follow a change in pH based on the concentration of the target agent in the solution.

A titrant is mixed in known increments with a sample from the solution, the sample having an unknown concentration of a target chemical agent, and an "indicator," until a given reaction point, for example color change, is produced. The reaction point is typically termed the "endpoint," and is directly indicative of the concentration of the target chemical agent in the solution, as is discussed in greater detail below. The analysis of the chemical agent is automated so that numerous concentration readings may be performed and analyzed over the course of a source run (the period during which the solution containing the unknown concentration of chemical agent is being used to accomplish its predetermined goal). A corrective action may be taken when the titration provides results showing that the target chemical agent concentration is outside a series of predetermined parameters.

A chemical analysis is used to elicit the chemical agent's concentration in the solution. As is known in the art, a typical chemical analysis involves adding a known concentration of an s oxidizing agent, i.e., an agent that oxidizes, to an unknown concentration of a reducing agent, i.e., an agent that reduces, (or vice versa). Typically, an indicator having a distinctive colored reaction product serves to show the endpoint of the chemical reaction, i.e., the point at which the electrons lost by the oxidized species equals the number of electrons gained by the reduced species. The "indicator" in the chemical reaction typically has a distinctive color in one oxidative state as compared to other oxidative states. By knowing the concentration and volume of the known chemical agents, as well as the balanced equation for the chemical reaction, one can determine the concentration of the unknown or target chemical agents by following the distinctive color change of the indicator. Alternatively, as discussed in greater detail below, a standard curve using similar experimental conditions with known amounts of both titrant and target chemical agent may be plotted, to provide a relationship between the amount of titrant required to reach the endpoint of a known amount of target chemical agent (see below).

An appropriate enzyme or catalytic device can be added to the solution being tested so as to reduce the background levels of species that interfere with the chemical agent being tested. For example, catalase enzyme or platinum can be added to a solution being tested for peracid levels (biocide levels) so as to reduce the background levels of hydrogen peroxide but not substantially effect the peracid levels. The reduction in hydrogen peroxide levels helps minimize its effects on the chemical analysis, thereby providing a more distinct endpoint of the chemical reaction.

This system could also be used to measure more than one species in a solution. For example, hydrogen peroxide could be determined in the first step of the titration and peracid could be determined in the second step of the titration.

FIG. 1 illustrates a system 106 for controlling the concentration of a chemical agent in a source according to an embodiment of the present invention. A sample pump 108 receives a signal from a controller 110 to initiate the determination of the chemical agents concentration in the sample source 112. The sample pump 108 may flush out a reaction cell 114 with a volume of solution from the sample source 112. The flush of the reaction cell 114 may be accomplished by flushing from 20 to 50 volumes of solution through the reaction cell 114. The flush should be adequate to remove residual reactants, i.e., indicator, residual solution sample, in the reaction cell 114 from any previous use. Solution from the sample source 112 is flushed through the reaction cell 114 through the combined effort of the sample pump 108, which continually fills the reaction cell with solution and either a self primed drain pump 118, aspirator or simple gravity overflow for removal of the solution.

After the reaction cell 114 has been flushed, the reaction cell 114 is filled with solution to a predetermined level, termed the "flushing level" 120. The flushing level 120 is typically near the top of the reaction cell 114 but may be modified dependent on the available sample source sizes and reaction volumes. A drain pump 118 is either self-activated or activated by the controller to remove solution from the reaction cell 114 until the solution volume corresponds to a predetermined level in the reaction cell 114, termed the "monitoring level" 122. Note that the removal of solution from the reaction cell may also be accomplished by gravity overflow, for example by actuating a relief valve located at the monitoring level 122 or other like means. The monitoring level 122 represents a predetermined amount of solution to be tested on that particular run, i.e., one determination/modification of the target chemical agent's concentration, of the system 106. The solution that fills the reaction cell to the monitoring level 122 is referred to as the solution sample 116. As with the flushing level 120, the monitoring level 122 can be altered between determinations of chemical agent concentration dependent on, for example, available sample volume, reaction parameters, etc. The monitoring level 122 in the reaction cell 114 provides a precisely regulated reaction volume for the volumetric titration that is not dependent upon adding predetermined volumes of solution to the reaction cell 114, where residual solution may add up in the reaction cell 114 and change the reaction volume of the volumetric titration. Typical sample sizes, as determined by the monitoring level 122, are from 2 to 100 mls, and preferably from 10 to 20 mls.

The reaction cell 114 is preferably, i.e., where an optical characteristic is being followed, a light permeable reaction vessel having the capacity to hold a liquid. In one embodiment of the present invention, the reaction cell is a flow cell or cuvet. Other types of reaction cells are within the scope of the invention as long as the cell is complementary with the system 106.

A reaction stirrer 124 is activated by the controller 110 during or soon after the sample 116 is delivered to the reaction cell 114. The reaction stirrer 124 is typically a magnetic stirring device located below the reaction cell, having a Teflon™ coated stir bar within the reaction cell. The speed and timing of a reaction's stirring is controlled by the controller and may be manipulated dependent upon reaction volume and speed with which the reagents 126 must be combined during a chemical agent detection run. Alternatively, the reaction stirrer 124 may be a stand alone device that is manually turned on and left on during the entire course of a run or runs, thereby not receiving or dependent upon a signal from the controller 110. Note that the reaction stirrer 124 may also be or include a shaft stirrer, recirculation pump or other like devices.

In one embodiment, a light-emitting diode (LED) 128/photosensor 130 (termed the second photosensor) assembly measures the initial light intensity of the sample. (see also FIG. 3) The LED 128 emits light at a wavelength of from 380 nm to 800 nm through the reaction cell 114. The second photosensor 130 receives the light and measures the received lights intensity and transmits this information to the controller 110. This initial reading of the sample in the reaction cell 114 is the baseline (comparison point) mV response or I(hi) (see below).

A reagent pump 132 receives a signal from the controller 110 to add a set of reagents 126 to the sample 116 in the reaction cell 114. Reagents 126 are typically used in a titration in order to optimize the sensitivity and precision of the detection of the target chemical agent in the sample source 112, and so numerous different reagent combinations may be used dependent on the target chemical agent, sample source and indicator chemistries. Titrations are based on a chemical reaction whereby the concentration of the chemical agent may be determined by adding a solution of known volume and strength until a reaction point is reached, usually indicated by a color change (see below). One example of a titration chemistry for use with the present invention is shown in FIG. 2 where the concentration of a biocide, e.g., peracid, may be detected in process water. An unknown concentration of peracid ($CH_3COOOH$) from a sample source is reacted with $I^-$ to form an unknown amount of $I_3^-$, which is further reacted with starch to form a dark blue $I_3^-$/starch complex. This portion of the reaction takes place when the reagents are added to the reaction cell. As discussed more fully below, a known amount of titrant ($2S_2O_3^{2-}$) (reducing agent) is then added to the reaction cell where it reacts with the colored $I_3^-$/starch complex to dissociated $I_3^-$/starch complex to a colorless $3I^-$ and starch mixture. The reaction produces a color change from dark blue ($I_3^-$/starch complex) to colorless ($3I^-$ plus starch) which is followed by the LED (128) and the second photosensor (130) until the endpoint of the reaction is reached. Other titration chemistries can be used in conjunction with the present invention. Titrations depend on the mode of detection, i.e., optical characteristic, pH, conductivity, etc, so that a method of the present invention may also utilize NaOH as the titrant and detect a change in the sample with a pH meter as well as other known means within the art.

Still referring to FIG. 2, the reagents 126, for the presently illustrated embodiment, can include an acid ($H^+$) to modify the reaction pH to between 1 and 4, and an indicator ($3I^-$ and starch) to sharply define the endpoint. Acids for use with the reaction illustrated in FIG. 2 include, but are not limited to, phosphoric acid, hydrochloric acid, sulfuric acid, etc. The preferable acid is phosphoric acid ($H_3PO_4$). One preferable combination of reagents for detecting peracids using the chemical reaction illustrated in FIG. 2 is to have a sample that contains 53% phosphoric acid, 10% potassium iodide and 2% starch solution. Further, a catalyst may be added to facilitate one or more aspects of the target chemical reaction, for example, ammonium molybdate may be used to facilitate the redox reaction or catalase enzyme can be used to reduce the background of hydrogen peroxide.

Preferably, the combined reagents 126 are mixed together into one solution for addition to the reaction cell 114, and hence the solution sample 116. Surprisingly, sequential addition of each reagent to the reaction cell has proven to be less accurate, yielding larger data standard deviations.

Referring again to FIG. 1, the reagents 126 are mixed with the solution sample 116 for a predetermined amount of time by the action of the reaction stirrer 124. If the sample contained peracid, the potassium iodide reacts with the peracid to form a carboxylic acid, water and iodine ($I_3^-$). (see FIG. 2). The iodine further reacts with the starch to form a complex having a dark blue color. It is important that the peracid is the limiting reagent so that all the peracid has reacted to form a quantitative amount of iodine/starch complex. After the reagents 126 react with any peracid in the sample, a second reading is taken through the reaction cell 114 by the LED 128/photosensor 130 assembly to measure the light intensity in mV, this is often termed the I(lo) point (see below).

After the I(lo) reading has been communicated to the controller 110, a signal is sent by the controller 110 to trigger a titrant pump 134 to add titrant to a titrant dropper 138. The titrant pump 134 is activated and removes a predetermined amount of titrant from the titrant reservoir 140 and fills the titrant dropper 138. A preferable amount of titrant for addition to the titrant dropper 138 is between 1 and 2 milliliters (mls). The titrant used to illustrate the embodiment of the present invention in FIG. 2 is sodium thiosulfate ($Na_2S_2O_3$). Note that as the sodium thiosulfate is added to the reaction cell it reacts with the dark blue iodine/starch complex to form colorless reaction products, $I_3^-$ and $S_4O_6^{2-}$. The addition of titrant continues until the endpoint, or other such target point, of the reaction is reached. The endpoint of the reaction indicates the point where a known concentration of titrant causes a determinable number of electrons to be gained or lost from the target species, associated with a distinctive color change (dark blue to colorless in the example discussed in FIG. 2).

Again referring to FIG. 1, addition of titrant 136 to the reaction cell occurs when individual drops of titrant 136 are released from the titrant dropper 138 into the reaction cell 114, and hence solution sample 116/reagent mixture. A LED 142/photosensor 144 (termed the first photosensor) assembly detects the number of drops 136 released from the titrant dropper 138 by detecting each drop as an interruption of light—causing a substantial pulse of light for each drop that falls from the titrant dropper 138 into the reaction cell 114. A pulse counter 143 relays the information to the controller 110 and counter 147. In preferable embodiments, the release of each drop 136 of titrant is timed so that the drop is fully mixed into the solution sample 116/reagent 126 mixture and a reading made by the LED 128/photosensor 130 before the next drop of titrant is released. One embodiment for facilitating the delay is to have a valve 146 in the titrant dropper 138 that is responsive to a signal from the controller 110. As titrant is added to the reaction cell, the LED 128/130 is continually transmitting the light intensity of the solution sample within the reaction cell to the controller 110.

Figure 3:
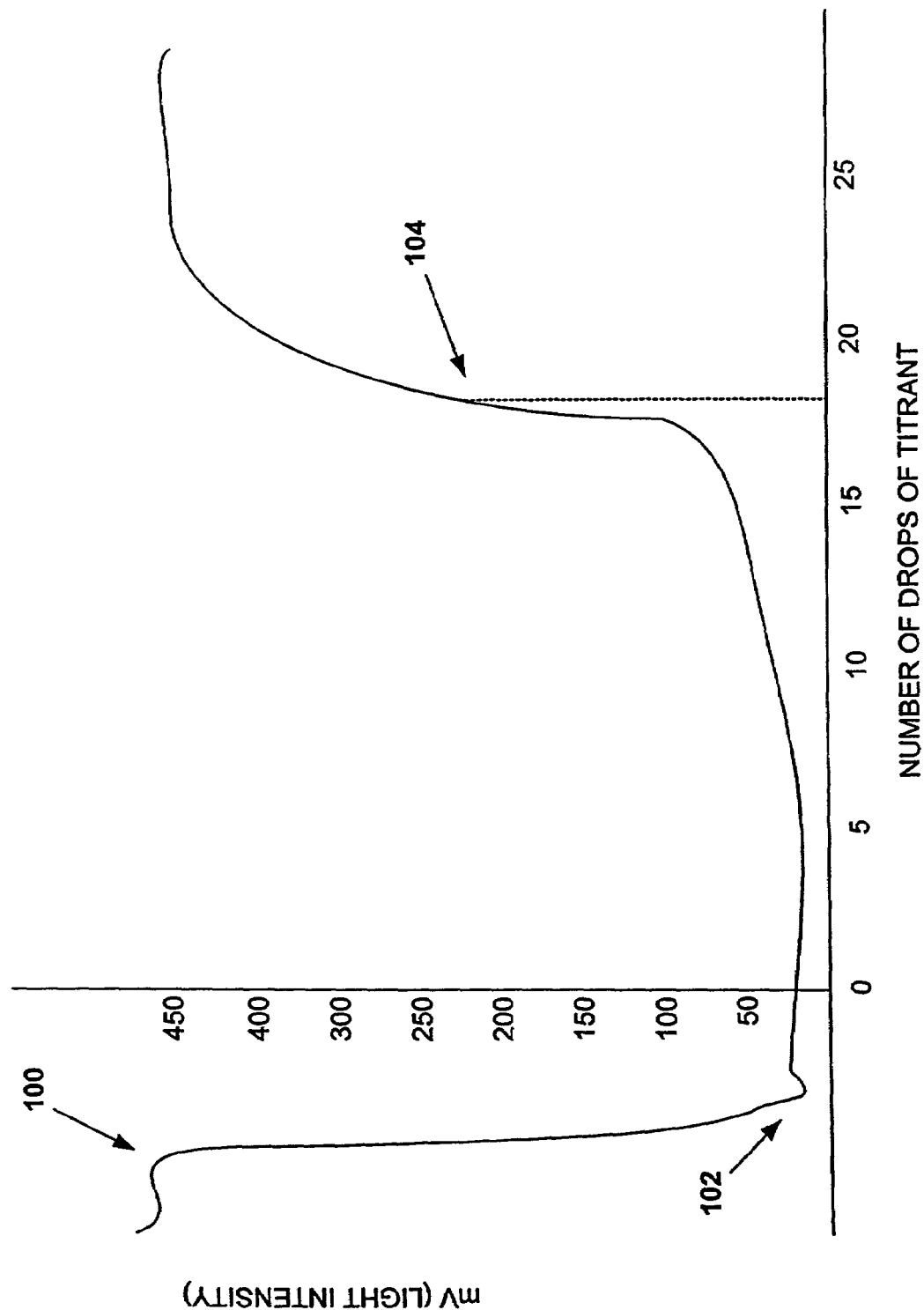
FIG. 3 illustrates a representative titration curve showing the endpoint of one potential chemical reaction in accordance with the present invention.

FIG. 3 illustrates a graphical representation of a titration using an optical characteristic, i.e., light intensity, to follow the reaction. Using the chemical reaction discussed in FIG. 2, in the absence of reagents, the solution sample allows the majority of light to pass through to the second photosensor 130, as indicated by arrow 100 (I(hi)). Addition of reagents 126 causes the peracid in the sample to induce the formation of a dark blue complex, e.g., $I_3$/starch complex, as indicated by arrow 102 (I(lo)). The dark blue complex causes a drastic reduction in the light intensity detected at the second photosensor 130. Addition of titrant to the sample causes the dark blue complex to react and form a colorless solution. As the colorless reaction species are formed, more light is detected by the second photosensor until the endpoint is reached, as indicated by arrow 104.

Again referring to FIG. 1, once the endpoint is reached the controller 110 signals the titrant pump 134 to turn off. Note that the endpoint is any reproducible point that avoids noise at the transition region, for example, at $\frac{1}{2}[I(hi)+I(lo)]$, $\frac{1}{3}[I(hi)+I(lo)]$, highest point of the $1^{st}$ derivative of the curve, and the like, and can be in a linear or log scale.

Figure 4:
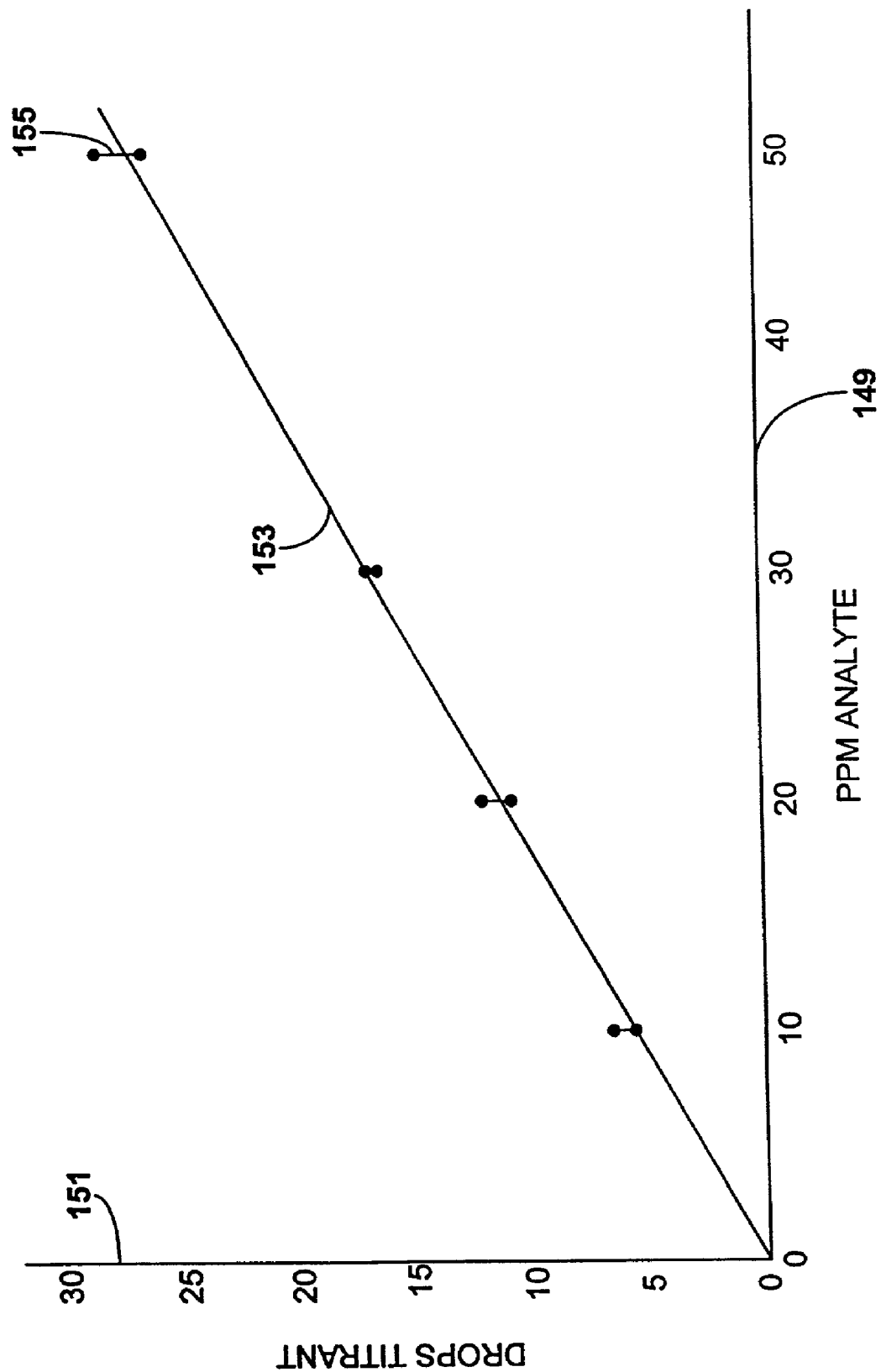
FIG. 4 illustrates a representative curve used to determine the final concentration of a target chemical agent in a sample in accordance with the present invention.

Once the controller 110 has determined the amount of titrant required to reach the endpoint of the reaction, it may send a signal to the reaction stirrer 124 to turn off. A second drain pump (not shown) or waste valve may be activated to remove the test sample. In preferred embodiments, a post flush of sample or water may be used to minimize any lingering starch or other contaminant in the reaction cell. The number of drops of titrant required to reach the endpoint of the reaction may then be compared to "standard curve" data stored in the memory of the controller 110. Note, the standard curve data stored in the controller 110 is determined by having previously taken a series of samples, each sample having a sequentially larger concentration of the target chemical agent, and testing each sample on the system 106. The number of drops of titrant required to reach the endpoint (as determined by light intensity) or any standardized points of light intensity, for each sample is plotted to provide a relationship between chemical agent concentration and drops of titrant required to reach the endpoint. As shown in FIG. 4, parts per million of a chemical agent 149 in a sample are plotted against the number of titrant drops 151 required to reach the endpoint 153 for that chemical agent under the reaction conditions, and repeated for accuracy 155. The data plot is referred to as a standard curve and is stored in a table in memory in the controller 110. The controller 110 takes the data in memory and determines the unknown concentration of the target chemical agent from the number of drops of titrant required to reach the endpoint of the reaction. In preferred embodiments, a parametric fit, e.g., linear least square, is performed and a conversion performed by equation with the parameters determined from the fit. Note, as discussed previously, other standard curve data can be stored in the controller 110, for example, the number of drops of titrant in relation to a target pH, etc.

A user interface 148 is alerted at the completion of a sample run and the concentration results of the chemical agent are displayed. Results can be transmitted to a field operator, to an operation facility, or to a central data base for future use, etc. For example, a central data base 157 can be created having data from previous sample runs. The stored data can be generated from the same or other like sources and can be used as a comparison point for tracking the performance of the system 106 at controlling the chemical agent's levels in the source, for tracking the efficiency of how much chemical agent is added to the source as compared to how well the source's chemical agent levels have been controlled, i.e., the efficiency of sample run. The generated results from the sample run can be compared to the data in the central data base to determine if additional supplies need to be obtained for future runs/treatments, as well as like circumstances.

When the concentration of the chemical agent is below or above certain predetermined critical parameters an alarm can be triggered, for example, if the chemical agent is at a toxic concentration in the sample source 112, an alarm is set off, and optionally the sample source 112 drained. In a preferred embodiment, the user interface 148 can transmit manual instructions from the user to the controller 110. For example, the user may request that the sample run be repeated, concentration parameters altered, sample size adjusted, etc.

When the analyte concentration in the sample 116, and hence the sample source 112, is below a predetermined parameter, the controller 110 determines a corrective amount of agent to be added to the sample source 112. Controller 110 signals a dosing pump 150 to pull the corrective amount of agent from a supply 152 and release it into the sample source 112. Release of the agent is controlled into the sample source 112 to quickly and safely change the agent's concentration. When the chemical agent concentration in the solution sample 116, and hence the sample source 112, is above a predetermined parameter, the controller 110 determines the corrective dilution required to bring the existing agent's concentration within the predetermined parameters. Controller 110 signals the dosing pump 150 to pull the corrective amount of water or other non-agent containing solution 154 from a supply and release it into the sample source 112.

Figure 5:
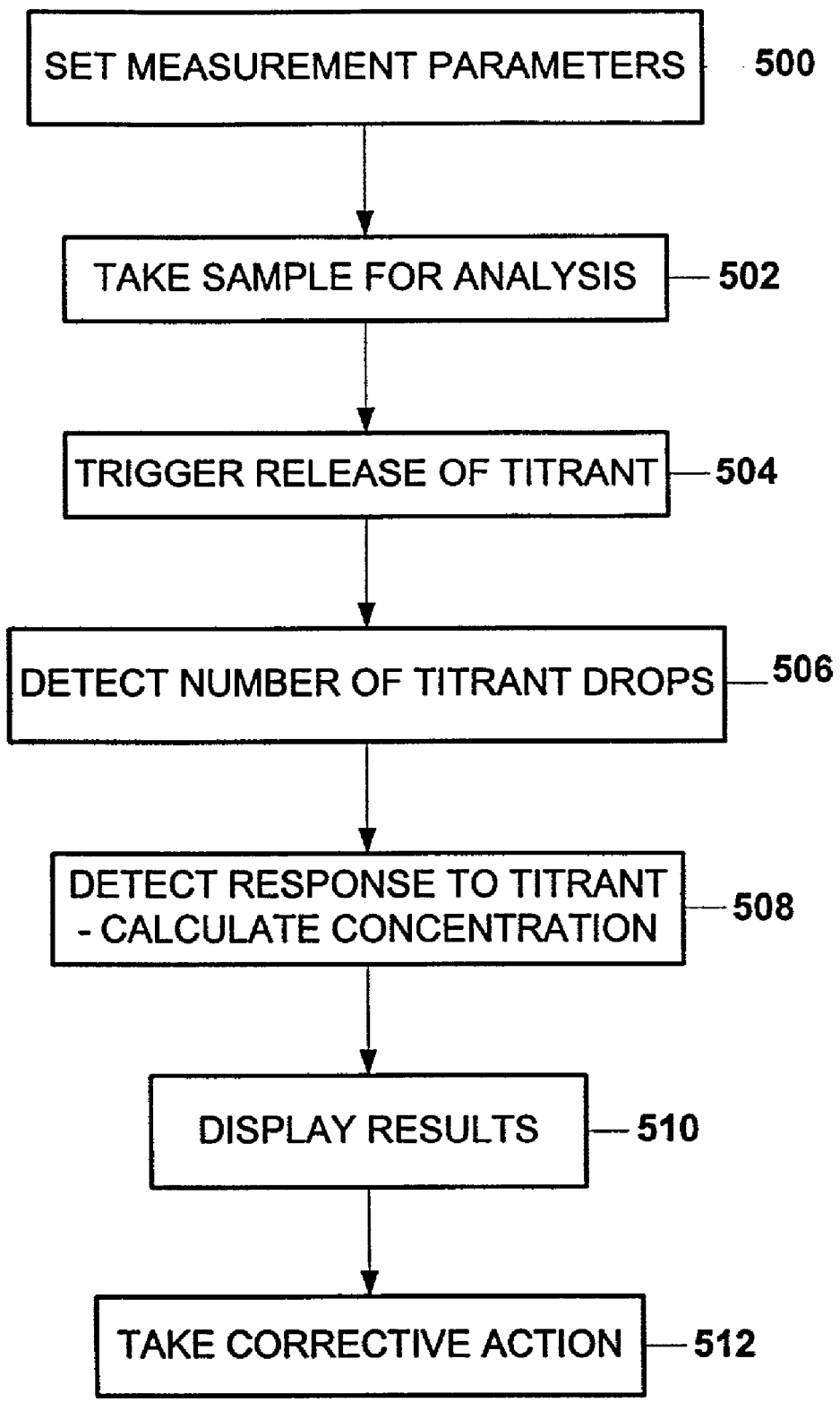
FIG. 5 illustrates operations taken to control the chemical agent concentration in a sample source in an embodiment of the present invention.

One method in accordance with a preferred embodiment of the present invention is shown in FIG. 5. In operation 500, the parameters for the target chemical agent are set and input into the controller. Parameters include, for example, the sample size, reaction chemistry, the concentration of each reagent and volume of reagent required for each sample run, titrant concentration and volume of titrant to be loaded into the titrant dropper, delay time between each drop of titrant release, standard curve conversion between the number of titrant drops and the target agent concentration, the range for acceptable sample chemical agent concentrations, dosing data for corrective action, etc.

Operation 502 assumes control from operation 500. In operation 502, solution of appropriate volume is removed from the sample source for analysis, and a sample added to the reaction cell. The sample is mixed with the appropriate reagents for analysis. Operation 502 surrenders control to operation 504. In operation 504, release of a titrant is triggered. The titrant is released one drop at a time so that the titrant drop falls into the sample. In one embodiment of the present method there is a sufficient delay between the release of each drop of titrant to allow the titrant to be mixed into the sample and a reading made of the sample. One embodiment for this delay is a valve in the titrant dropper that is triggered at appropriate preset intervals. Operation 506 assumes control from operation 504. In operations 506 and then operation 508, the release of a drop of titrant is detected and transmitted to the controller as a counted drop, while the response to the drop of titrant in the sample is monitored. A preset reaction point, for example the endpoint, is compared by the controller to the monitored data received from the sample. When the preset reaction point is the same or within a preset range of the reaction point, the concentration of target chemical agent is calculated from the number of drops of titrant released into the sample. Operation 510 assumes control from operation 508. In operation 510, a result from the run is displayed on a user interface. Operation 512 assumes control from operation 510. In operation 512, a determination is made as to whether corrective action is required to either dilute or concentrate the agent's concentration in the sample source. In one embodiment, the chemical agent is automatically released as a result of the determined concentration.

Figure 6:
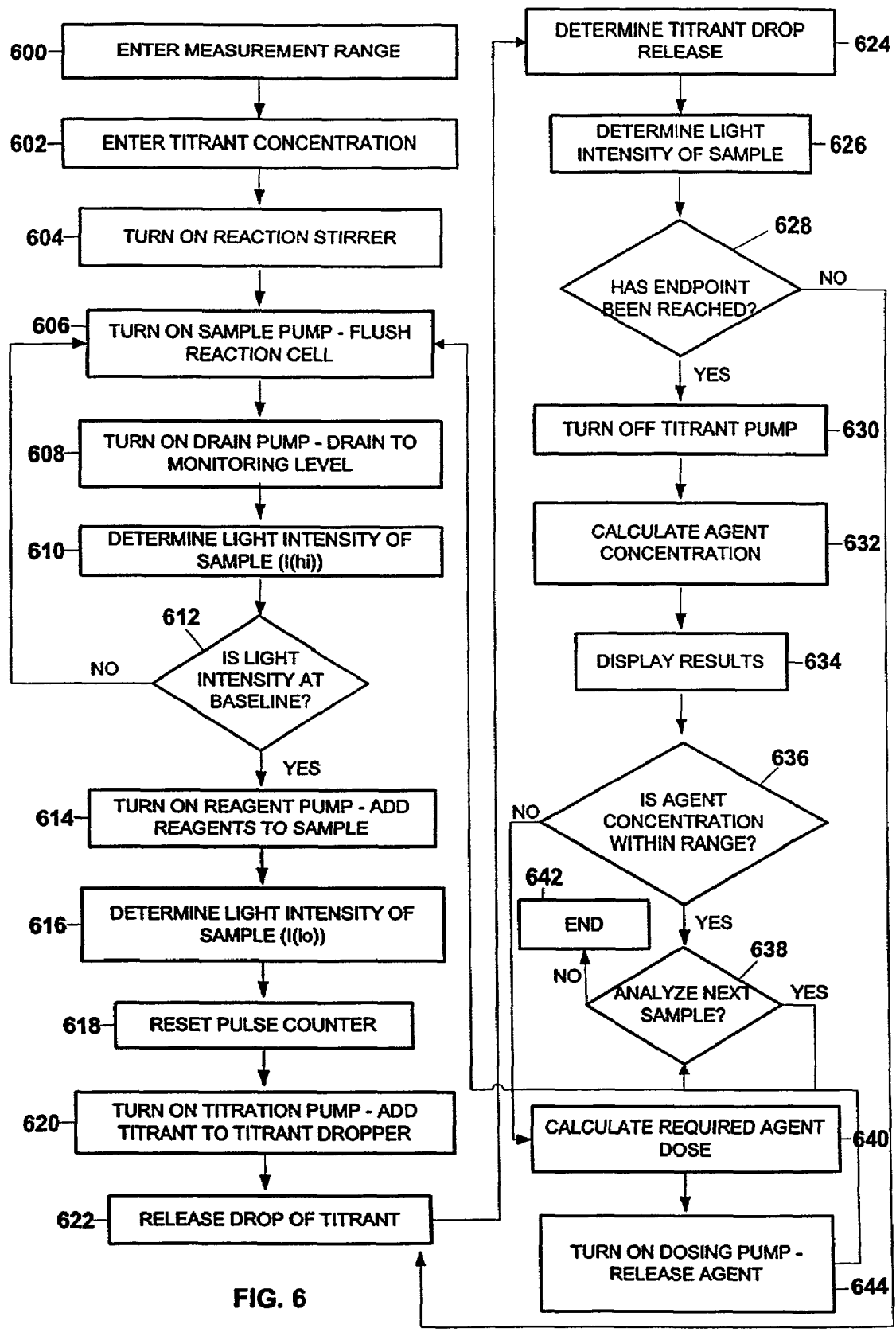
FIG. 6 illustrates detailed operations taken to control the chemical agent concentration in a sample source in an embodiment of the present invention.

Another method in accordance with a preferred embodiment of the present invention is shown in FIG. 6. In operation 600, the measurement range for the next sample run is entered from either a preset menu of existing standardized ranges or new ranges entered. The ranges may be automatically entered, i.e., use last data unless commanded otherwise, or may require a manual command for each sample run. Operation 602 assumes control from operation 600. In operation 602, the concentration of the titrant is entered. Preferably, the information obtained in operations 600 and 602 is sufficient to calculate a target chemical agent concentration from a number of titrant drops required to reach an endpoint for a particular titration run.

Operation 604 assumes control from operation 602. In operation 604, the reaction stirrer is turned on to a preset speed. Sample volume size, titrant concentration, length of delay between release of each titrant drop, viscosity of the sample, etc, are factors in determining the reaction stirrer's set speed. Alternatively, a default speed may be set and used to accommodate the most extreme reaction conditions. Operation 606 assumes control from operation 604. In operation 606, the sample pump is activated and solution is taken from the sample source and flushed through the reaction cell. The amount of solution flushed through the reaction cell is preset, and dependent on the size of the reaction cell, sample size, flow time, flow rate, sensitivity required for the chemical analysis, etc. The solution can be flushed through the reaction cell either passively, by allowing the solution to flow out of the reaction cell, or actively by siphoning or pumping the excess solution from the reaction cell as the reaction cell fills. Operation 608 assumes control from operation 606. In operation 608, the drain pump is activated and solution removed from the reaction cell until a preset volume of sample remains for testing.

After operation 608 is completed, operation 610 assumes control. In operation 610, the light intensity through the sample is ascertained. The light intensity reading is the baseline (I(hi)) for further readings made on the sample during the course of the analysis. (see FIG. 3) In an embodiment of the present method, a determination operation 612 ascertains whether the light intensity of the sample is within a preset range of light intensity. A lower than expected light intensity suggests either a damaged light source or reaction cell, i.e., scratched glass, smudged glass, etc, or possibly that contaminates from previous reactions remain in the reaction cell. Operation control branches YES if the light intensity of the sample is within the appropriate range and operation control is assumed by operation 614. Operation control branches NO if the light intensity of the sample is not within the appropriate range and operation 606 assumes control. If operation control branches NO a second time in a row, operation control switches to operation 642, and the system is switched off.

In operation 614, the reagent pump is activated and a preset volume of reagent is added to the reaction cell. Operation 614 delays for a preset period of time to allow the added reagents to mix with the sample before surrendering control to operation 616. In operation 616, the light intensity is ascertained for the sample/reagent mixture (I(lo)). (see FIG. 3) Operation 618 assumes control from operation 616. In operation 618 the pulse counter is reset.

Operation 620 assumes control from operation 618. Operation 620 triggers the titration pump to add titrant to the titrant dropper. Optionally, operation 620 may control a valve in the titrant dropper to regulate the release of each drop of titrant. Operation 622 assumes control from operation 618, a drop of titrant is released from the titrant dropper into the sample.

Operation 624 assumes control from operation 622. Operation 624 detects the drop of titrant released from the titrant dropper which is relayed to the pulse counter. The pulse counter counts the drop and relays the information to the controller/counter. Operation 626 assumes control from operation 624. In operation 626, the light intensity of the sample/reagent/titrant mix is determined. Operation 626 delays before ascertaining the light intensity so that the titrant is properly mixed into the reaction mixture, and the reaction allowed to come to an equilibrium. After operation 626 is completed, determination operation 628 ascertains whether the endpoint (or other reaction stop point) has been reached. Operation control branches YES if the light intensity is within a predetermined range from the light intensity endpoint (½(I(hi)+I(lo)) or other endpoints that avoid noise at the transition point) and control is surrendered to operation 630. Operation control branches NO if the light intensity is below the predetermined range from the light intensity endpoint and operation 622 assumes control. This cycle will continue until results allow operation control to branch YES.

Operation 630 assumes control from operation 628 to turn off the titrant pump and in embodiments with a titrant valve, to close the valve in the titrant dropper. Operation 632 assumes control from operation 630. Operation 632 assimilates the number of drops of titrant required to reach the endpoint of the reaction with preset data from standard curves or other analyte conversions, to calculate the concentration of target analyte in the sample and hence the sample source. Operation 634 assumes control from operation 632 and displays the chemical agent concentration for viewing by a field worker, facility manager or other interested user. After operation 632 is complete, determination operation 636 ascertains whether the sample source agent concentration is within the preset ranges. Operation control branches YES if the agent concentration is within preset ranges and determination operation 638 assumes control. Operation control branches NO if the agent concentration is not within preset ranges and operation 640 assumes control.

Determination operation 638 ascertains whether multiple determinations for each sample are required. Operation control branches YES where a next reading is required at some future time. Variable delay periods may be present with operation control, so that a next sample is analyzed in 1 minute, 5 minutes, 15 minutes or any other desirable interval. When the delay period has expired operation control is surrendered to operation 606. Operation control branches NO where a next reading is not required and operation 642 assumes control. Operation 642 turns off the reaction stirrer, sample pump, drain pump, light sources, pulse counter, and display.

When operation 640 has assumed control, operation control determines the amount of chemical agent required, or the dilution factor needed, to bring the agent's concentration within predetermined agent concentrations. Operation 644 assumes control from operation 640 once the appropriate corrective action has been determined. In operation 644, the dosing pump is activated to release either chemical agent, to concentrate the chemical agent concentration, or water (or other sample compatible liquid), to dilute the chemical agent concentration, into the sample source. Once complete, operation 638 assumes control from operation 644.

It will be clear that the present invention is well adapted to attain the ends and advantages mentioned as well as those inherent therein. While a presently preferred embodiment has been described for purposes of this disclosure, various changes and modifications may be made which are well within the scope of the present invention. Numerous other changes may be made which will readily suggest themselves to those skilled in the art and which are encompassed in the spirit of the invention disclosed and as defined in the appended claims.

What is claimed is:

1. A system comprising:
   a reaction cell that receives a sample of a source solution containing a concentration of a chemical agent;
   a reagent pump that adds reagents to the reaction cell once the reaction cell has received the sample;
   a titrant dropper that releases one or more drops of titrant into the reaction cell once the reaction cell has received the reagents, wherein the titrant changes a characteristic of the sample;
   a sensor that detects the number of drops of titrant released into the reaction cell;
   a controller in communication with the reagent pump, the titrant dropper, and the sensor, wherein the controller computes the concentration of the chemical agent in the sample based on the number of drops of titrant released in the sample and a corresponding change in the characteristic of the sample; and
   a dosing pump in communication with the controller, wherein:
      the controller commands the dosing pump to add chemical agent to the source solution when the controller determines that the concentration of the chemical agent in the sample is below a predetermined value; and
      the controller commands the dosing pump to add a diluting agent to the source solution when the controller determines that the concentration of the chemical agent in the sample is above a predetermined value.

2. The system of claim 1 further comprising:
   a sample pump in communication with the controller, wherein the controller operates the sample pump to pump the sample of the source solution into the reaction cell.

3. The system of claim 1 further comprising:
   a drain pump in communication with the controller, wherein the controller operates the drain pump to remove source solution from the reaction cell until the sample reaches a predetermined level within the reaction cell.

4. The system of claim 1 further comprising:
   a titrant pump in communication with the controller, wherein the titrant pump adds titrant to the titrant dropper when the controller determines that the reagent pump has added the reagents to the reaction cell.

5. The system of claim 1 wherein the sensor comprises a first photosensor and a light source, wherein the first photosensor senses a disruption in light received from the light source for every drop of titrant released by the titrant dropper into the reaction cell.

6. The system of claim 5 wherein the characteristic of the sample that is changed by the titrant comprises a color of the sample, the system further comprising:
   a second photosensor that receives light transmitted through the sample and communicates changes in light intensity to the controller, wherein the controller associates changes in the light intensity with the concentration of the chemical agent in the sample.

7. The system of claim 1 further comprising a user interface in communication with the controller that displays the computed concentration of chemical agent in the source solution.

8. The system of claim 7 wherein the user interface is at a remote location separate from the controller.

9. The system of claim 8 wherein the remote location is an operation facility.

10. The system of claim 7 further comprising a central data base in communication with the controller, wherein the computed value of the concentration of the chemical agent is stored in the central data base and compared with previously stored measurements to track the efficiency of the system in maintaining a desired concentration of the chemical agent in the source solution.

11. The system of claim 1 wherein, when the controller determines that the concentration of the chemical agent is below a predetermined value, the controller further determines the amount of chemical agent required to raise the concentration of the chemical agent to the predetermined value.

12. The system of claim 11 wherein the controller compares the amount of chemical agent required to raise the concentration of the chemical agent to the predetermined value with an amount of available chemical agent and provides a signal to a user interface when the available amount of the chemical agent is less than the required amount.

13. The system of claim 1 wherein the diluting agent is water.

14. The system of claim 1 wherein the chemical agent is a peracid and the source solution is process water.

15. The system of claim 14 wherein the process water is for sanitizing fruits and vegetables.

16. The system of claim 14 wherein the process water is for disinfecting surfaces of polyethylene terephthalate (PET) bottles.

17. The system of claim 1, wherein the controller commands the dosing pump to a corrective amount of the chemical agent to the source solution when the controller determines that the concentration of the chemical agent in the sample is below the predetermined value.

18. The system of claim 17, wherein the controller determines the corrective amount of the chemical agent based on the concentration of the chemical agent in the sample.

19. The system of claim 1, wherein the controller commands the dosing pump to add a corrective amount of a diluting agent to the source solution when the controller determines that the concentration of the chemical agent in the sample is above a predetermined value.

20. The system of claim 19, wherein the controller determines the corrective amount of the diluent agent bused on the concentration of the chemical agent in the sample.

21. The system of claim 6, wherein the second photosensor receives light transmitted through the sample wherein the light source is a light-emitting diode (LED) emitting light at a wavelength of from 380 nm to 800 nm.

22. The system of claim 1 wherein the chemical agent is a biocide.

23. The system of claim 22 wherein the biocide is a peracid.

24. The system of claim 1 wherein the chemical agent is a disinfectant.

25. The system of claim 1 wherein the characteristic of the sample comprises one of an optical characteristic of the sample, a color of the sample, a pH of the sample, or a conductivity of the sample.

26. The system of claim 1 wherein the titrant is NaOH and the characteristic of the sample is a pH of the sample.

27. The system of claim 1 wherein the characteristic of the sample is a pH of the sample and further including a pH meter to detect a change in the pH of the sample.

* * * * *

UNITED STATES PATENT AND TRADEMARK OFFICE
CERTIFICATE OF CORRECTION

| | | |
|---|---|---|
| PATENT NO. | : 7,349,760 B2 | Page 1 of 1 |
| APPLICATION NO. | : 10/099494 | |
| DATED | : March 25, 2008 | |
| INVENTOR(S) | : Wei et al. | |

It is certified that error appears in the above-identified patent and that said Letters Patent is hereby corrected as shown below:

Page 2, OTHER PUBLICATIONS, please add -- Bran and Luebbe Monitor 90 S Analyzers Handbook --

Signed and Sealed this

First Day of January, 2013

David J. Kappos
*Director of the United States Patent and Trademark Office*